United States Patent [19]

Dudzinski et al.

[11] 4,282,215
[45] Aug. 4, 1981

[54] ANALGESIC MIXTURE OF NALBUPHINE AND ACETYLSALICYLIC ACID, DERIVATIVE OR SALT THEREOF

[75] Inventors: John R. Dudzinski, East Northport, N.Y.; William K. Schmidt, Wilmington, Del.

[73] Assignee: E. I. Du Pont de Nemours and Company, Wilmington, Del.

[21] Appl. No.: 170,931

[22] Filed: Jul. 28, 1980

Related U.S. Application Data

[63] Continuation-in-part of Ser. No. 160,437, Jun. 17, 1980, abandoned, which is a continuation-in-part of Ser. No. 69,083, Aug. 23, 1979, abandoned.

[51] Int. Cl.$^3$ .......................................... A61K 31/625
[52] U.S. Cl. .................................................. 424/232
[58] Field of Search ......................................... 424/232

[56] References Cited

U.S. PATENT DOCUMENTS 3,393,197  7/1968  Pachter ................................ 424/260

*Primary Examiner*—Stanley J. Friedman

[57] ABSTRACT

A composition consisting essentially of nalbuphine and acetylsalicylic acid, derivative or salt thereof, gives unexpectedly enhanced analgetic activity.

24 Claims, 2 Drawing Figures

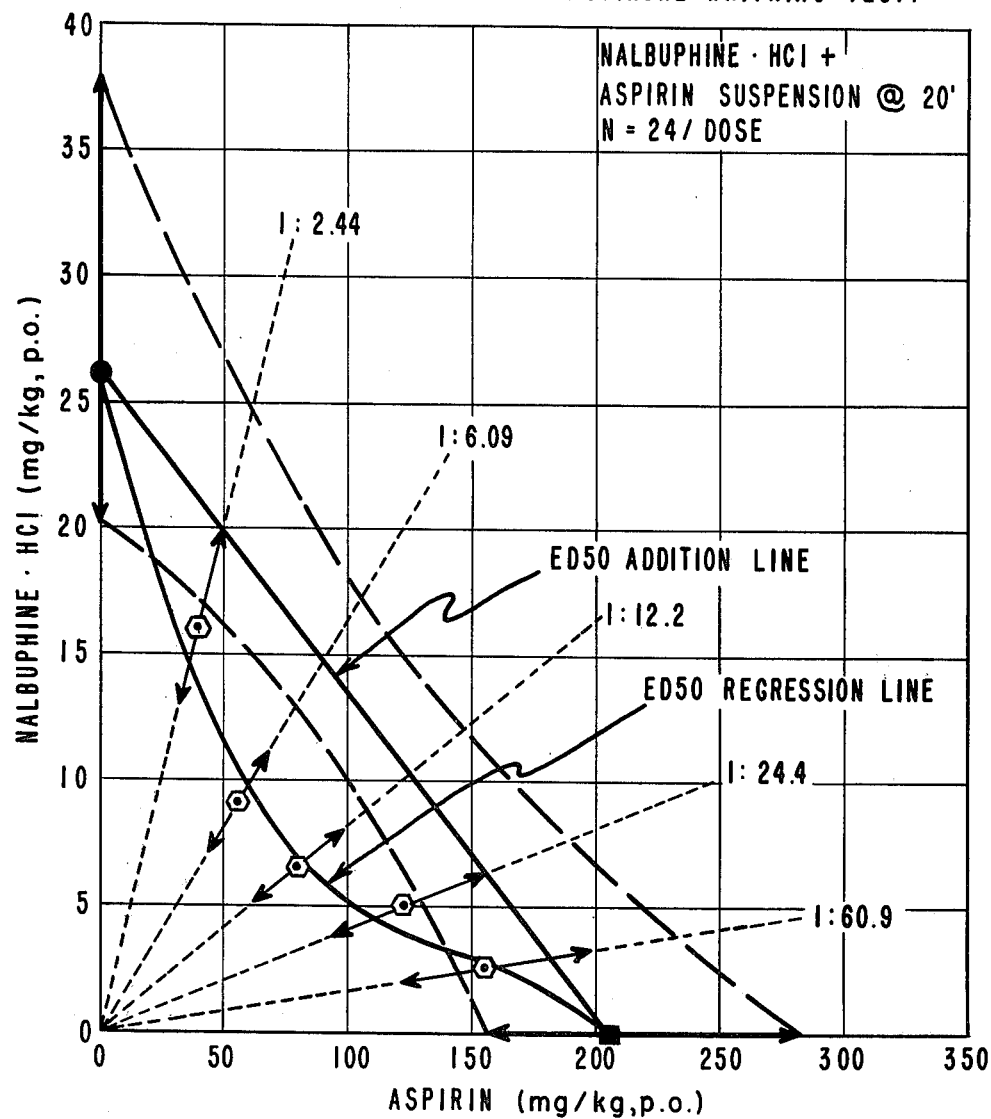

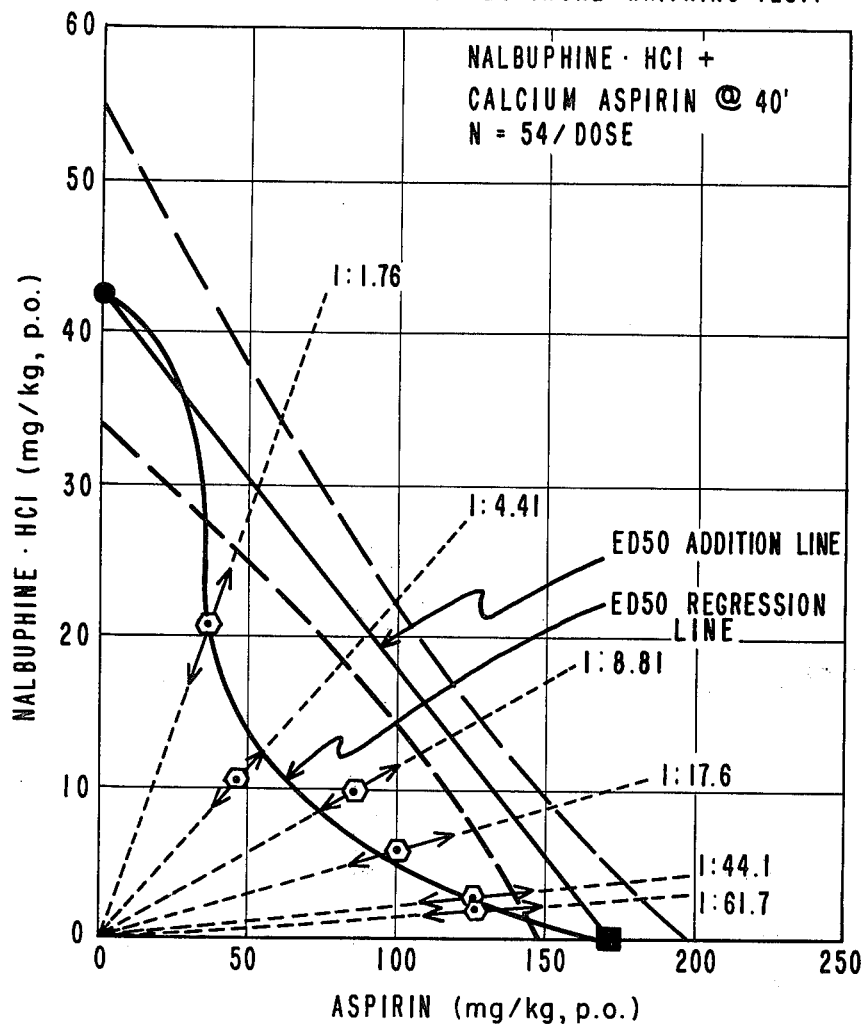

ANALGESIC MIXTURE OF NALBUPHINE AND ACETYLSALICYLIC ACID, DERIVATIVE OR SALT THEREOF

CROSS-REFERENCE TO RELATED APPLICATIONS

This application is a continuation-in-part of application Ser. No. 160,437 filed on June 17, 1980, now abandoned, which in turn is a continuation-in-part of application Ser. No. 69,083 filed on Aug. 23, 1979, now abandoned.

BACKGROUND OF THE INVENTION

This invention relates to a pharmaceutical combination of compounds having analgetic activity.

U.S. Pat. No. 3,393,197 issued to Pacheter and Matossian on July 16, 1968 discloses N-substituted-14-hydroxydihydronormorphines, including the N-cyclobutylmethyl derivatives, commonly called nalbuphine:

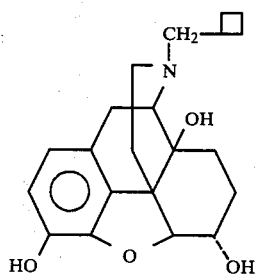

Pachter and Matossian and others, such as H. W. Elliott, et al., *J. Med.* (Basel), 1, 74–89 (1970); H. Blumberg, et al., *Pharmacologist*, 10, 189, Fall 1968; P. Roberts, *Drugs of the Future*, 2, 613–5 (1977), disclose the use of nalbuphine as an analgesic for the control of moderate to severe pain.

D. M. Woodbury and E. Fingl, "Analgesic-antipyretics, Anti-inflammatory Agents, and Drugs Employed in the Therapy of Gout," in "The Pharmacological Basis of Therapeutics," 5th edition, Macmillan Publishing Co., Inc., 1975, pp. 325–358, report that oral combinations of acetylsalicylic acid, also known as aspirin, with codeine or with other narcotic analgesics are known to produce additive analgesic effects in man.

U.S. Pat. No. 4,049,803, issued to Cotty et al. on Sept. 20, 1977, discloses a composition for oral administration comprising per dose a mixture containing about 5–15 grains of acetaminophen and about 10 grains of acetylsalicylic acid. The composition gives increased blood levels of unhydrolyzed aspirin.

More active analgesic combinations are in constant demand because they offer the attractive possibility of relieving pain with reduced dosages, thereby diminishing the expected side effects and toxicity that would result from the otherwise required higher dosages.

SUMMARY OF THE INVENTION

According to the present invention there is provided an analgesic composition consisting essentially of (a) nalbuphine or a pharmaceutically suitable acid addition salt thereof and (b) acetylsalicylic acid, sodium acetylsalicylate, calcium acetylsalicylate, salicylic acid, or sodium salicylate or any combination thereof in a weight ratio of (a) to (b) of from about 1:1.76 to about 1:61.7. There are also provided methods of using said composition to alleviate pain in mammals.

BRIEF DESCRIPTION OF THE DRAWING

FIGS. 1 and 2 are graphs showing the interaction of nalbuphine and the herein specified acetylsalicylic acid, derivatives or salts thereof on phenyl-p-benzoquinone induced writhing in mice.

DETAILED DESCRIPTION OF THE INVENTION

Nalbuphine, which has the chemical name (−)17-(cyclobutylmethyl)-4,5α-epoxymorphinan-3,6α,14-triol, the pharmaceutically suitable addition salts of nalbuphine, particularly the hydrochloride, and acetylsalicylic acid, derivatives or salts thereof, as described herein, all have analgetic properties in man and in other mammals.

As used herein, the expression "acetylsalicylic acid, derivatives or salt thereof" means and is limited to acetylsalicylic acid, sodium acetylsalicylate, calcium acetylsalicylate, salicylic acid and sodium salicylate. This group of compounds or any one of the group shall be hereinafter sometimes referred to by the acronym, ASA. Although it is expected that the alumimum salt of acetylsalicylic acid and salicylamide may also provide unexpectedly enhanced activity in combination with nalbuphine, they have not been included within the definition because of their minimal commercial value. Preferably the ASA compound is acetylsalicylic acid, sodium acetylsalicylate or calcium acetylsalicylate, and, most preferably is acetylsalicylic acid or its sodium salt.

In the composition of the invention nalbuphine or a pharmaceutically suitable acid addition salt thereof and ASA are combined in a weight ratio of nalbuphine to ASA of from about 1:1.76 to about 1:61.7 preferably, from about 1:3 to about 1:50, and most preferably from 1:12 to 1:45, respectively. It has been found that when these compounds are combined in these ranges, the resulting composition gives unexpectedly enhanced analgetic activity, i.e., the resulting activity is greater than the activity expected from the sum of the activities of the individual components. Compositions within the preferred range give the highest analgetic activity.

The composition of the invention presents the opportunity of obtaining relief from pain with reduced dosages of nalbuphine and ASA, thereby diminishing the side effects and toxicity which would result from the otherwise required amounts of the individual drug components.

DOSAGE FORMS

The combination of analgetic agents of the invention can be administered to treat pain by any means that produces contact of the active agent with the agent's site of action in the body of a mammal. The composition of the invention can be administered by any conventional means available for use in conjunction with pharmaceuticals. It can be administered alone, but is generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage can be such that the active ingredient is administered at a daily dosage of from about 0.25 to 7.50 milligrams per kilogram (mg/kg) of body weight of nalbuphine and from about 10.8 to 54 mg/kg of ASA. Ordinarily, administration of the composition of the invention in divided doses 2–5 times per day or in sustained release form is effective to obtain desired results.

Dosage forms (compositions) suitable for internal administration contain from about 50 milligrams to about 600 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

Suitable pharmaceutical carriers are described in *Remington's Pharmaceutical Sciences*, E. W. Martin, a standard reference text in this field.

Useful pharmaceutical dosage-forms for administration of the composition of the invention can be illustrated by the following examples in which the word "aspirin" refers to acetylsalicylic acid.

EXAMPLE 1

| Nalbuphine/Aspirin Tablets | |
|---|---|
| Formula (1:43) | 7.5/325 mg/Tablet |
| | mg/Tablet |
| Nalbuphine . HCl | 7.50 |
| Aspirin | 325.00 |
| Lactose Anhydrous | 229.80 |
| Microcrystalline Cellulose | 200.00 |
| Sterotex ® hydrogenated vegetable oil | 7.70 |
| TOTAL | 770.00 mg |

A large number of tablets can be prepared by conventional methods, utilizing the formula above.

EXAMPLE 2

| Nalbuphine/Aspirin Tablets | |
|---|---|
| (a) Formula (1:16) | 20/325 mg/Tablet |
| | mg/Tablet |
| Nalbuphine . HCl | 20.00 |
| Aspirin | 325.00 |
| Lactose, Anhydrous | 217.30 |
| Microcrystalline Cellulose | 200.00 |
| Sterotex ® hydrogenated vegetable oil | 7.70 |
| TOTAL | 770.00 mg |
| (b) Formula (1:8) | 40/325 mg/Tablet |
| Nalbuphine/Aspirin Tablets | |
| | mg/Tablet |
| Nalbuphine . HCl | 40.00 |
| Aspirin | 325.00 |
| Lactose, Anhydrous | 197.30 |
| Microcrystalline Cellulose | 200.00 |
| Sterotex ® hydrogenated vegetable oil | 7.70 |
| TOTAL | 770.00 mg |

A large number of tablets can be prepared by conventional methods, utilizing the formulas above.

EXAMPLE 3

| Nalbuphine/Aspirin Capsules | |
|---|---|
| (a) Formula (1:43) | 7.5/325 mg/Capsules |
| | mg/CAP |
| Nalbuphine . HCl | 7.50 |
| Aspirin | 325.00 |
| Lactose, Anhydrous | 95.90 |
| Starch | 6.60 |
| TOTAL | 435.00 mg |
| (b) Formula (1:16) | 20/325 mg/Capsules |
| | mg/CAP |
| Nalbuphine . HCl | 20.00 |
| Aspirin | 325.00 |
| Lactose, Anhydrous | 83.40 |
| Starch | 6.60 |
| TOTAL | 435.00 mg |
| (c) Formula (1:8) | 40/325 mg/Capsules |
| | mg/CAP |
| Nalbuphine . HCl | 40.00 |
| Aspirin | 325.00 |
| Lactose, Anhydrous | 63.40 |
| Starch | 6.60 |
| TOTAL | 435.00 mg |

A large number of unit capsules may be prepared by filling standard two-piece hard gelatin capsules with the above formulations utilizing conventional techniques.

UTILITY

Test Methods

The unexpectedly enhanced analgetic activity of the composition of the invention is evidenced by tests conducted on mice. Male $CF_1$ mice obtained from Charles River Breeding Laboratories, fasted for 16–22 hours, and weighing 18–22 g at the time of testing are used throughout. All mice are dosed sequentially by the oral route with suspensions of acetylsalicylic acid and/or of nalbuphine solutions (Method 1) or of calcium acetylsalicylate (calcium aspirin) and/or of nalbuphine solutions (Method 2). In each case the aspirin component is calculated as the equivalent free acid content, and nalbuphine is calculated as the hydrochloride salt. A dosing volume of 10 ml/kg is used for each sequential solution or suspension. All doses are coded and the test is performed under a code not known to the observer.

Method 1: Sequential combinations of aspirin suspensions and nalbuphine.HCl

A stock suspension of aspirin is prepared by mixing 2.016 gm aspirin with 40 ml of an aqueous vehicle containing 2% by volume of Tween 80 ®, a pharmacological dispersant manufactured by Fisher Scientific Company and containing 100% polysorbate 80, and 1% by weight of Methocel ® MC powder, a pharmacological suspending agent manufactured by DOW Chemical Company and containing 100% methylcellulose, in distilled water. The mixture is sonicated at 150 watts for 10-15 seconds with an ultrasound system, then shaken for 1 hour at 280 oscillations/minute with 15-20 gm of glass beads. The resultant suspension contains 50.4 mg/ml of aspirin; all dosing suspensions are prepared by dilution of the stock suspension with the Methocel ®/Tween 80 ® vehicle; the vehicle control is Methocel ®/Tween 80 ®. All suspensions are used within two hours of preparation, then discarded.

Stock solutions of nalbuphine.HCl are prepared by dissolving dry nalbuphine hydrochloride powder with distilled water. All dosing solutions are prepared by dilution of the stock solutions with distilled water; the vehicle control is distilled water.

Method 2: Combinations of calcium aspirin and nalbuphine.HCl

A stock solution of calcium aspirin is prepared by mixing 4.032 gm of aspirin and 1.120 gm of precipitated calcium carbonate with 50 ml of distilled water at 40°-50° C. until the solids are completely dissolved, then diluting to 60 ml with distilled water at ambient temperature to obtain a solution containing 67.2 mg/ml of aspirin equivalent. All dosing solutions are prepared by dilution of the stock solution with distilled water; the vehicle control is distilled water. All solutions are used within two hours of preparation, then discarded.

Stock solutions of nalbuphine.HCl are prepared as described for Method 1.

ANALGETIC ACTIVITY IN THE MOUSE ANTIPHENYLQUINONE WRITHING TEST

A standard procedure for detecting and comparing the analgetic activity of different classes of analgesic drugs for which there is a good correlation with human analgetic activity is the prevention of phenyl-p-benzoquinone induced writhing in mice [H. Blumberg et al., *Proc. Soc. Exp. Biol. Med.*, 118, 763-766 (1965)].

Mice, intubated with various doses of nalbuphine.HCl, aspirin suspensions (Method 1), calcium aspirin solution (Method 2), or immediately sequential doses of nalbuphine.HCl and of the aspirin preparations as defined further, or of the respective vehicles, are injected intraperitoneally with a standard challenge dose of phenyl-p-benzoquinone 5 min. prior to a designated observation period. The phenyl-p-benzoquinone is prepared as a 0.1 mg/ml solution in 5% by volume of ethanol in water; the writhing dose is 1.25 mg/kg injected at a volume of 0.25 ml/20 g. For scoring purposes a "writhe" is indicated by whole body stretching or contraction of the abdomen during a 10 min. observation period beginning 5 min. after receiving the phenyl-p-benzoquinone dose. Each mouse is used only once, then discarded.

All ED50 values and their 95% confidence limits are determined numerically by the methods of Thompson [W. F. Thompson, *Bacteriological Rev.*, 11, 115-145 (1947)], Litchfield and Wilcoxon [J. T. Litchfield, Jr. and F. Wilcoxon, *J. Pharm. Exp. Ther.*, 96, 99-113 (1949)], or Finney [D. J. Finney, "Probit Analysis," third edition, Cambridge University Press, Cambridge, England, (1971)]. As used herein in ED50 means the dosage at which 50% of the mice in a test group exhibit an analgetic response.

The interaction of nalbuphine.HCl and aspirin suspensions on phenyl-p-benzoquinone induced writhing in mice is demonstrated by the data in Table 1 and by the Loewe isobologram [S. Loewe, *Pharm. Rev.*, 9, 237-242 (1957)] in FIG. 1. The interaction between nalbuphine.HCl and calcium aspirin solutions is demonstrated in Table 2 and by the Loewe isobologram in FIG. 2. In the isobolographic figures, the analgetic effects of nalbuphine alone are presented on the Y axis and of aspirin alone (or calcium aspirin, expressed as aspirin equivalent dosages) on the X axis. The dotted lines radiating from the origin represent the fixed dosage ratios of nalbuphine.HCl:aspirin in the ranges of 1:2.44 to 1:60.9 and 1:1.76 to 1:61.7 for FIGS. 1 and 2, respectively. ED50 values representing the calculated dosages where 50% of a group of animals would be expected to exhibit an analgetic response are marked on the Y and X axes, representing nalbuphine and aspirin ED50's alone, and on the dotted radial lines, representing the nalbuphine and aspirin components of the fixed dosage ratios. The arrows extending above and below each ED50 point represent the 95% confidence limits of the ED50's.

The solid line connecting the ED50 dosages of nalbuphine (alone) and aspirin (alone) represents the "ED50 addition line," which indicates the expected location of the ED50's for nalbuphine and aspirin combinations if simple additivity were to describe their combined effects. The 95% confidence range for the ED50 addition line is shown by the area between the broken lines above and below the ED50 addition line. According to Loewe's isobolographic theory, if the analgetic effects of nalbuphine and aspirin were simply additive to one another, the expected location for the ED50's of the nalbuphine and aspirin components of each fixed dosage ratio would be contained within, or overlap, the region of the ED50 addition line. Combination ED50's located significantly below the ED50 addition line would represent unexpectedly enhanced analgetic activity and combination ED50's located above the line would represent unexpectedly diminished analgetic activity.

One method to establish the significance of such unexpected enhanced or diminished activity is to calculate the best fitting polynominal regression line to the observed ED50's using standard mathematical techniques. This "ED50 regression line" is represented in FIGS. 1 and 2 by the curvilinear line connecting all of the ED50 points within their 95% confidence limits. For FIG. 1 the following equation applies:

$$Y = 5.762 - 0.08112\ (X-93.83) + 0.0009289\ (X-93.83)^2 - 0.00000594\ (X-93.83)^3$$

where Y represents the ED50 dosage component of nalbuphine and X represents the ED50 dosage component of aspirin. For FIG. 2 the equation given below applies:

$$X = 56.62 - 4.476\ (Y-11.77) + 0.3168\ (Y-11.77)^2 - 0.0075\ (Y-11.77)^3$$

In both cases, analysis of variance demonstrates that the quadratic regressions are significantly different from the ED50 addition lines at the level of $P < 0.05$. Therefore, an unexpectedly enhanced analgetic response can be proven in a mathematically rigorous model utilizing the entire body of data to demonstrate that a curvilinear regression line encompassing the ED50's of each fixed dosage ratio fits the data significantly better than the linear ED50 addition line.

While the linear regression analysis demonstrates unexpected enhancement of the analgetic response and predicts that unexpectedly enhanced analgetic activity occurs in theory for all possible combinations of nalbuphine and aspirin, the statistical significance for the endpoint ratios of nalbuphine and aspirin that were actually tested may be proven using either the "Least Significant Differences" or the "Studentized Q method" tests described by Snedecor and Cochran [G. W. Snedecor and W. G. Cochran, "Statistical Methods," sixth edition, Iowa State University Press, Ames, Iowa (1967)]. The "expected ED50's" may be read from the graph or alternatively may be calculated by using the formula:

$$Y = \frac{Y_o}{1 + \frac{1-R}{ZR}}$$

where Y is the expected ED50 for the nalbuphine component of a mixture, $Y_o$ is the ED50 for nalbuphine alone, Z is the potency ratio between aspirin and nalbuphine, and R is the ratio of nalbuphine in the total drug composition $T = X + Y$. Similarly, the expected ED50 for the aspirin component is found according to:

$$X = Y\left(\frac{1-R}{R}\right)$$

Thus, using the data in Table 2 and FIG. 2:

| COMBINATION Nalbuphine:Aspirin | TOTAL DOSE Expected ED50 (95% Conf. Limits) | Observed ED50 (95% Conf. Limits) | Significance |
|---|---|---|---|
| 1:61.7 | 163 mg/kg (143–186) | 129 mg/kg (111–150) | P < 0.05 |
| 1:1.76 | 81.7 mg/kg (70.7–94.5) | 57.4 mg/kg (49.1–67.0) | P < 0.05 |

Unexpectedly enhanced analgetic activity can also be proven by showing that the net analgetic response produced by a drug mixture is greater than predicted from the sum of individual responses of the components. Thus, using the data in Table 1:

| COMBINATION Nalbuphine:Aspirin | DOSE (mg/kg) Nalbuphine | Aspirin | RESPONSE Expected | Observed |
|---|---|---|---|---|
| 1:12.2 | 5.18 | 63 | 8.3% | 29.2% |
| | 10.4 | 126 | 54.2% | 83.3% |
| | 20.7 | 252 | ~100% | 95.8% |
| | 41.4 | 504 | ~100% | 100% |

In this case, the 1:12.2 drug ratio is the only one where the combination dosages are exactly the same as dosages found in the individual component tests. For the two lowest dosages tested, the observed percentage response is clearly greater than the expected response. For the two highest dosages tested, the expected response would actually exceed 100% by summation of the effects of the individual component dosages; since the observed response cannot actually exceed 100%, enhancement cannot be measured even though it has most likely occurred with these dosages as well. Using this method, responses that differ by less than 5% can not be considered to be significantly different from each other; thus, a response rate of 95.8% in the observed column is not significantly less than a 100% response rate.

Similarly, using the date from Table 2:

| Nalbuphine:Aspirin | DOSE (mg/kg) Nalbuphine | Aspirin | RESPONSE Expected | Observed |
|---|---|---|---|---|
| 1:8.81 | 5.45 | 48 | 20.4% | 16.7% |
| | 10.9 | 96 | 29.7% | 50.0% |
| | 21.8 | 192 | 90.8% | 98.1% |
| | 43.6 | 384 | ~100% | 98.1% |

In this situation, the 1:8.81 drug ratio is the only one where the combination dosages are exactly the same as dosages found in the individual component tests. For the two mid-range dosages tested, the observed percentage response is clearly greater than the expected response. For the highest dosage tested, the observed response is again limited by the restraint that it connot exceed a 100% response rate; however, enhancement of the analgetic response has most likely occurred here as well (a 98.1% response is not significantly different from a 100% response using this method). For the lowest dosage tested, analgetic synergism was not observed; however, for reasons previously given, a 16.7% response is not significantly different than a 20.4% response.

This conventional method would also be expected to show unexpected enhanced analgetic activity for all of the other dosage ratios tested, but since none of the other dosages are identical with the dosages in the individual component tests, the actual test of significance cannot be performed.

Therefore, FIGS. 1 and 2 and a variety of statistical approaches show that compositions of the invention having a ratio of nalbuphine.HCl to aspirin from about 1:1.76 to 1:61.7 given unexpectedly enhanced analgetic activity.

The isobolographic technique, rather than the technique using the sum of the individual component responses, has been used in establishing enhancement for several reasons. First, this technique allows the use of a full range of doses and the calculation of ED50's and 95% confidence limits for these doses whereas in the conventional method, i.e., the method of comparing the sum of the individual component responses to the response of the combination, the maximum response must be limited to less than 50% for each component. If, in this conventional method, the individual responses are not less than 50%, then it will not be possible to measure enhancement.

Secondly, with the isobolographic technique statistical significance is straightforward and can be seen graphically. The calculation of statistics for the technique of using the sum of the individual component responses is more involved. Thirdly, for certain ratios the isobolographic technique as utilized here gives also a presentation of evidence of enhancement via use of the sum of the individual component responses, thereby providing additional corraboration of the results.

TABLE 1

ORAL NALBUPHINE . HCl/ASPIRIN SUSPENSION COMBINATIONS IN THE MOUSE ANTIPHENYLQUINONE WRITHING TEST AT 20 MINUTES
(N = 24 Mice/Dose)

| DRUG COMBINATIONS Nalbuphine . HCl: Aspirin | DRUG DOSE (mg/kg) Nalbuphine . HCl | Aspirin | % MICE BLOCKED | ED50 at 20 MIN. (95% Confidence Limits) Nalbuphine . HCl | Aspirin |
|---|---|---|---|---|---|
| (Control) 0:0 | 0 | 0 | 0% | — | — |
| (Nalbuphine . HCl only) 1:0 | 5.18 | 0 | 0% | 26.1 mg/kg (20.0–38.1) | |
| | 10.4 | 0 | 16.7% | | |
| | 20.7 | 0 | 50.0% | | |
| | 41.4 | 0 | 62.5% | | |
| 1:2.44 | 4.31 | 10.5 | 4.2% | 16.0 mg/kg (13.0–19.7) | 39.1 mg/kg (31.6–48.1) |
| | 8.63 | 21. | 16.7% | | |
| | 17.3 | 42. | 45.8% | | |
| | 34.5 | 84. | 91.7% | | |
| | 69.0 | 168. | 100.0% | | |
| 1:6.09 | 3.45 | 21. | 8.3% | 9.04 mg/kg (7.44–10.9) | 55.1 mg/kg (45.3–66.7) |
| | 6.90 | 42. | 20.8% | | |
| | 13.8 | 84. | 79.2% | | |
| | 27.6 | 168. | 100.0% | | |
| | 55.2 | 336. | 100.0% | | |
| 1:12.2 | 2.59 | 31.5 | 8.3 | 6.49 mg/kg (5.26–7.97) | 79.0 mg/kg (64.0–97.0) |
| | 5.18 | 63. | 29.2% | | |
| | 10.4 | 126. | 83.3% | | |
| | 20.7 | 252. | 95.8% | | |
| | 41.4 | 504. | 100.0% | | |
| 1:24.4 | 1.73 | 42. | 8.3% | 5.01 mg/kg (3.98–6.31) | 122 mg/kg (97.0–154) |
| | 3.45 | 84. | 25.0% | | |
| | 6.90 | 168. | 70.8% | | |
| | 13.8 | 336. | 91.7% | | |
| 1:60.9 | 0.86 | 52.5 | 4.2% | 2.55 mg/kg (2.02–3.25) | 155 mg/kg (123–198) |
| | 1.73 | 105. | 29.2% | | |
| | 3.45 | 210. | 79.2% | | |
| | 6.90 | 420. | 83.3% | | |
| (Aspirin only) 0:1 | 0 | 63. | 8.3% | — | 206 mg/kg (154–284) |
| | 0 | 126. | 37.5% | | |
| | 0 | 252. | 58.3% | | |
| | 0 | 504. | 79.2% | | |

TABLE 2

ORAL NALBUPHINE . HCl/CALCIUM ASPIRIN* COMBINATIONS IN THE MOUSE ANTIPHENYLQUINONE WRITHING TEST AT 40 MINUTES
(N = 54 Mice/Dose)

| DRUG COMBINATIONS Nalbuphine . HCl: Aspirin | DRUG DOSE (mg/kg) Nalbuphine . HCl | Aspirin | % MICE BLOCKED | ED50 at 40 MIN. (95% Confidence Limits) Nalbuphine . HCl | Aspirin |
|---|---|---|---|---|---|
| (Control) 0:0 | 0 | 0 | 5.6% | — | — |
| (Nalbuphine only) 1:0 | 5.45 | | 13.0% | 42.6 mg/kg (32.9–55.1) | — |
| | 10.9 | 0 | 16.7% | | |
| | 21.8 | 0 | 27.8% | | |
| | 43.6 | 0 | 50.0% | | |
| | 87.2 | 0 | 74.1% | | |
| 1:1.76 | 4.54 | 8 | 3.7% | 20.8 mg/kg (17.8–24.3) | 36.6 mg/kg (31.3–42.7) |
| | 9.08 | 16 | 16.7% | | |
| | 18.2 | 32 | 29.6% | | |
| | 36.3 | 64 | 83.3% | | |
| | 72.7 | 128 | 100.0% | | |
| 1:4.41 | 3.63 | 16 | 16.7% | 10.4 mg/kg (8.68–12.6) | 46.0 mg/kg (38.1–55.5) |
| | 7.27 | 32 | 33.3% | | |
| | 14.5 | 64 | 50.0% | | |
| | 29.1 | 128 | 98.1% | | |
| | 58.1 | 256 | 100.0% | | |
| 1:8.81 | 2.73 | 24 | 3.7% | 9.71 mg/kg (8.38–11.2) | 85.5 mg/kg (73.8–99.0) |
| | 5.45 | 48 | 16.7% | | |
| | 10.9 | 96 | 50.0% | | |
| | 21.8 | 192 | 98.1% | | |
| | 43.6 | 384 | 98.1% | | |
| 1:17.6 | 1.82 | 32 | 5.6% | 5.73 mg/kg | 101 mg/kg |
| | 3.63 | 64 | 20.4% | | |
| | 7.27 | 128 | 63.0% | | |

TABLE 2-continued

ORAL NALBUPHINE . HCl/CALCIUM ASPIRIN* COMBINATIONS
IN THE MOUSE
ANTIPHENYLQUINONE WRITHING TEST AT 40 MINUTES
(N = 54 Mice/Dose)

| DRUG COMBINATIONS Nalbuphine . HCl: Aspirin | DRUG DOSE (mg/kg) Nalbuphine . HCl | Aspirin | % MICE BLOCKED | ED50 at 40 MIN. (95% Confidence Limits) Nalbuphine . HCl | Aspirin |
|---|---|---|---|---|---|
| | 14.5 | 256 | 96.3% | (4.80–6.88) | (84.4–121) |
| | 29.1 | 512 | 100.0% | | |
| | 0.908 | 40 | 14.8% | | |
| 1:44.1 | 1.82 | 80 | 13.2% | | |
| | 3.63 | 160 | 64.8% | 2.85 mg/kg | 126 mg/kg |
| | 7.27 | 320 | 94.4% | (2.45–3.33) | (108–147) |
| | 14.5 | 640 | 100.0% | | |
| | 0.681 | 42 | 5.6% | | |
| | 1.36 | 84 | 22.2% | | |
| 1:61.7 | 2.73 | 168 | 64.8% | 2.07 mg/kg | 127 mg/kg |
| | 5.45 | 336 | 98.1% | (1.77–2.40) | (109–148) |
| | 10.9 | 672 | 98.1% | | |
| | 0 | 48 | 7.4% | | |
| (Aspirin only) | 0 | 96 | 13.0% | — | 171 mg/kg |
| | 0 | 192 | 63.0% | | (150–195) |
| 0:1 | 0 | 384 | 87.0% | | |

*All dosages of calcium aspirin are expressed in terms of equivalent free aspirin content

What is claimed is:

1. A pharmaceutical composition consisting essentially of (a) nalbuphine or a pharmaceutically suitable acid addition salt thereof and (b) acetylsalicylic acid, sodium acetylsalicylate, calcium acetylsalicylate, salicylic acid, or sodium salicylate or any combination thereof in a weight ratio of (a) to (b) of from about 1:1.76 to about 1:61.7.

2. A composition of claim 1 wherein component (b) is acetylsalicylic acid, sodium acetylsalicylate or calcium acetylsalicylate.

3. A composition of claim 2 wherein component (b) is acetylsalicylic acid.

4. A composition of claim 2 wherein component (b) is sodium acetylsalicylate.

5. A composition of claim 2 wherein component (b) is calcium acetylsalicylate.

6. A composition of claim 2 wherein the weight ratio is from about 1:3 to about 1:50.

7. A composition of claim 2 wherein the weight ratio is from about 1:12 to about 1:45.

8. A composition of claim 2 wherein the nalbuphine is present as the hydrochloride salt.

9. A composition of claim 1 which contains in addition a suitable pharmaceutical carrier.

10. A composition of claim 2 which contains in addition a suitable pharmaceutical carrier.

11. A composition of claim 3 which contains in addition a suitable pharmaceutical carrier.

12. A composition of claim 4 which contains in addition a suitable pharmaceutical carrier.

13. A composition of claim 5 which contains in addition a suitable pharmaceutical carrier.

14. A composition of claim 6 which contains in addition a suitable pharmaceutical carrier.

15. A composition of claim 7 which contains in addition a suitable pharmaceutical carrier.

16. A composition of claim 8 which contains in addition a suitable pharmaceutical carrier.

17. A method of alleviating pain in a mammal which comprises administering to the mammal an effective analgesic amount of the composition of claim 1.

18. A method of alleviating pain in a mammal which comprises administering to the mammal an effective analgesic amount of the composition of claim 2.

19. A method of alleviating pain in a mammal which comprises administering to the mammal an effective analgesic amount of the composition of claim 3.

20. A method of alleviating pain in a mammal which comprises administering to the mammal an effective analgesic amount of the composition of claim 4.

21. A method of alleviating pain in a mammal which comprises administering to the mammal an effective analgesic amount of the composition of claim 5.

22. A method of alleviating pain in a mammal which comprises administering to the mammal an effective analgesic amount of the composition of claim 6.

23. A method of alleviating pain in a mammal which comprises administering to the mammal an effective analgesic amount of the composition of claim 7.

24. A method of alleviating pain in a mammal which comprises administering to the mammal an effective analgesic amount of the composition of claim 8.

* * * * *